United States Patent
Schreijag et al.

(12) United States Patent (10) Patent No.: US 6,989,000 B2
(45) Date of Patent: Jan. 24, 2006

(54) SYRINGE, IN PARTICULAR FOR VETERINARY APPLICATIONS

(75) Inventors: Karl Schreijag, Rottwell (DE); Ralf Kiehn, Seitingen-Oberflacht (DE)

(73) Assignee: Henke-Sass, Wolf GmbH, Tuttlingen (DE)

(*) Notice: Subject to any disclaimer, the term of this patent is extended or adjusted under 35 U.S.C. 154(b) by 0 days.

(21) Appl. No.: 10/864,084

(22) Filed: Jun. 9, 2004

(65) Prior Publication Data
US 2005/0020983 A1 Jan. 27, 2005

(30) Foreign Application Priority Data
Jun. 11, 2003 (DE) .................. 103 26 306

(51) Int. Cl.
A61M 5/00 (2006.01)
A61M 5/178 (2006.01)

(52) U.S. Cl. .................. 604/68; 604/183; 604/191
(58) Field of Classification Search ........ 604/187–190, 604/191, 500, 183, 23, 68–70, 71
See application file for complete search history.

(56) References Cited

U.S. PATENT DOCUMENTS

| | | | | | |
|---|---|---|---|---|---|
| 3,908,651 | A | * | 9/1975 | Fudge .................. | 604/71 |
| 4,266,541 | A | * | 5/1981 | Landau ................. | 604/68 |
| 5,882,338 | A | | 3/1999 | Gray | |
| 6,394,982 | B1 | * | 5/2002 | Ehrenfels ............... | 604/191 |
| 6,645,181 | B1 | * | 11/2003 | Lavi et al. ............. | 604/191 |
| 2005/0107697 | A1 | | 5/2005 | Berke | |

FOREIGN PATENT DOCUMENTS

| | | |
|---|---|---|
| DE | 197 18 963 C1 | 2/1990 |
| DE | 197 11 605 C1 | 6/1998 |
| EP | 0 927 055 B1 | 12/2001 |
| WO | WO 02/070048 A1 | 9/2002 |

* cited by examiner

Primary Examiner—Nicholas D. Lucchesi
Assistant Examiner—Roz Maiorino
(74) Attorney, Agent, or Firm—Patterson, Thuente, Skaar & Christensen, P.A.

(57) ABSTRACT

A syringe for connection to a fluid container containing fluid to be discharged comprises a syringe barrel with a plunger moving therein, and a discharge outlet, through which fluid contained in the fluid container is dischargeable by actuation of the plunger, said syringe barrel being connected with the fluid container port and the discharge outlet via a fluid channel system, and a valve mechanism being provided in the fluid channel system, allowing the syringe barrel to be filled with fluid from the fluid container and to then discharge said fluid through the discharge outlet, wherein the valve mechanism comprises a valve member which is movable between first and second positions, said valve member, in said first position, allowing fluid flow from the fluid container to the syringe barrel and simultaneously blocking fluid flow from or to the discharge outlet and, in said second position, allowing fluid flow from the syringe barrel to the discharge outlet while simultaneously blocking fluid flow from or to the fluid container.

17 Claims, 6 Drawing Sheets

Fig. 6 though additionally providing a third position of the valve member at which the syringe barrel, the fluid container port and the discharge outlet are not in fluid

SYRINGE, IN PARTICULAR FOR VETERINARY APPLICATIONS

RELATED APPLICATION

This application claims priority to German Patent Application No. 103 26 306.3 filed Jun. 11, 2003.

TECHNICAL FIELD

The invention relates to a syringe comprising a fluid container port for a fluid container containing fluid to be discharged, a syringe barrel with a plunger moving therein, and a discharge outlet, through which fluid supplied by actuation of the plunger in the fluid container port is dischargeable, said syringe barrel being connected with the fluid container port and the discharge outlet via a fluid channel system, and a valve mechanism being provided in the fluid container port, allowing the syringe barrel to be filled with fluid supplied at the fluid container port and to then discharge said fluid through the discharge outlet.

BACKGROUND OF THE INVENTION

Particularly in veterinary applications, syringes are known which allow a syringe barrel to be filled repeatedly from a fluid container and to discharge the drawn fluid manually from the syringe barrel. This allows repeated injections of a precisely predetermined volume, as in the case of, for example, serial vaccinations or treatments of animals, and does not require the cumbersome filling of the syringe from a separate fluid container. The prior art syringes comprise two check valves. A first check valve is located between the syringe barrel and the discharge outlet and is connected such that fluid flow is possible only from the syringe cylinder to the discharge outlet, but not a counterflow such as might occur when drawing fluid from the fluid container connected with the syringe. A second check valve allows a fluid flow from the fluid container to the syringe barrel when pulling back the plunger, but not when advancing the plunger.

Such valve system is known for different fluid container systems. In a first construction, a fluid container is attached directly to the syringe, so that stored fluid flows into the syringe barrel by advancing the plunger. For this purpose, the fluid container is provided with a suitable pressure compensation mechanism preventing a vacuum from being generated within the fluid container. In a second variant, the fluid is contained under pressure and, when suitably released, automatically flows into the syringe barrel while pushing back the plunger. It is known to conduct a stop detection in these types of pressurefillable syringes, so that, when the syringe has been emptied, i.e. when the plunger is maximally advanced into the syringe barrel, the syringe barrel is automatically refilled, pushing back the plunger.

In particular, in the aforementioned second type of syringes, which are filled via a fluid container connected therewith, there may occur, during a filling operation, an undesired discharge of fluid through the discharge outlet, which is generally caused by the response behavior of the two check valves.

Therefore, it is the object of the invention to improve a syringe of the aforementioned type such that undesired discharges of fluid no longer occur during filling of the syringe barrel.

SUMMARY OF THE INVENTION

This object is achieved by a syringe of the aforementioned type, wherein the valve mechanism comprises a valve member which is movable between first and second positions, said valve member, in said first position, allowing fluid flow from the fluid container port to the syringe barrel and simultaneously blocking fluid flow from or to the discharge outlet and, in said second position, allowing fluid flow from the syringe barrel to the discharge outlet while simultaneously blocking fluid flow from or to the fluid container.

Thus, the invention no longer uses two independent check valves, but the closing of the discharge outlet and the opening of a filling opening, through which the syringe barrel may be filled with fluid from the fluid container, is effected by means of one single valve member moving between two positions. Accordingly, the closing of the discharge outlet and the opening of the supply opening for fluid flowing into the syringe barrel is effected by one single valve member, so that the occurrence of problems with differently responding check valves, each equipped with independent valve members, is positively eliminated. Moreover, a considerable simplification is achieved, because only one valve is required, which now serves the function of the two valves present in the prior art.

A particularly simple and compact structure is achieved by arranging the valve member in an opening region where a discharge channel from the syringe barrel to the discharge outlet and a duct from the fluid container to the syringe barrel converge. Switching between the first and second positions may then be achieved even by a very small movement of the valve member. A particularly simple construction is achieved if the valve member is displaceable between both positions.

Many useful alternatives which allow the first and second positions to be realized are suitable for the design of the valve member. For example, the valve member may be embodied in the form of a disk provided with suitable bores. However, it is particularly simple to manufacture a valve member having a first sealing surface, which closes the discharge channel to the discharge outlet in the first position, and having a second sealing surface, which closes the duct from the fluid container in the second position. Such sealing surfaces are technically rather easy to realize and allow a structure of the valve member comprising only few parts. This, of course, automatically leads to a simple assembly and disassembly. The latter aspect is advantageous bearing in mind that easy cleaning is required, in particular, for veterinary syringes.

The embodiment of the valve mechanism according to the invention comprising only one single valve member may be further improved by additionally providing a third position of the valve member at which the syringe barrel, the fluid container port and the discharge outlet are not in fluid communication with each other. This allows replacement, for example, of a needle attached to the discharge outlet or of the fluid container.

The third position of the valve member represents kind of a rest position, wherein the three components, namely the fluid container port, the syringe barrel and the discharge outlet, are separated from each other. Therefore, it is advantageous to provide a biasing means which urges the valve member toward the third position. In order to enable use of the syringe, the biasing means may be provided with a releasing means. Actuation of the syringe is particularly simple if the biasing means urges the valve member toward the third position in such a way that the resulting bias can be overcome by actuating the syringe plunger, thus moving the valve member into the second position. A separate device releasing the bias exerted by the biasing means is then dispensible; the user merely needs to move the syringe plunger in the usual way and may thus overcome said bias and move the valve member from the third into the second position.

In a particularly convenient embodiment of the invention, the biasing means is provided such that, when drawing further fluid from the fluid container, which may be effected either by the aforementioned pressure-filling or mechanically, the bias is also overcome and the valve member moves from the third to the first position.

In this respect, a construction which is particularly convenient, because it can be realized as a technically simple and easy-to-clean construction, is achieved if the valve member comprises an upper part with the first sealing surface and a lower part with the second sealing surface, said upper and lower parts being displaceable relative to one another and being pushed apart into the third position by the biasing means.

In order to keep the valve member easily accessible for cleaning purposes, it is preferred to arrange the valve member in a valve chamber, which forms one seat each for the first and second sealing surfaces of the valve member and into which a fluid channel opens, which extends to the syringe barrel. The valve chamber then forms the aforementioned opening region into which the ducts from the fluid container port, from the discharge outlet and from the syringe barrel extend.

The advantageous operation of the valve member of the syringe according to the invention is put to favourable use, in particular, by connecting the fluid container with a pressurizing means, allowing the fluid to be pressurized in order to fill the syringe barrel with fluid.

In applications where a large number of injections is to be carried out, as is common, for example, in veterinary medicine or in animal breeding, syringes are provided which are connectable to a fluid container holding a large quantity of fluid and from which said fluid is automatically drawn into the syringe barrel as soon as all injections have been performed, i.e. as soon as the plunger abuts within the syringe barrel upon being maximally advanced. In this connection, it is known to provide a stop-detecting device which recognizes an abutment of the plunger within the syringe barrel and transmits a corresponding signal to a control unit which then causes the syringe barrel to be refilled from the fluid container.

In most cases, this is effected by providing for a suitable pressure increase within the supply duct from the fluid container to the syringe barrel, for example, by pressurizing the fluid in the fluid container or by opening a valve to the fluid container holding pressurized fluid.

Mechanical switches are suitable to detect the stop position. It is also known in the prior art to measure the position of the plunger within the syringe barrel by means of a magnetic field sensor which, attached to the housing of the syringe, senses a magnetic unit, which may be formed, for example, by the plunger rod provided with a suitable magnetic structure. In a known working solution, a rotatable magnet assembly, which is supported on the housing of the syringe barrel and whose angular position is sensed by a magnetic field sensor also attached to the housing, is driven by the plunger rod via a gear unit.

These approaches allow precise sensing of the plunger position. Therefore, they are intended for syringes whose plunger is to be advanced by a predetermined length using a motor, in order to discharge a predetermined amount of fluid. However, the expenditure required in this connection is not necessary at all in detecting the stop position of the plunger. Therefore, these concepts have not been successful for syringes in which it is merely required to detect the stop position of the plunger at the bottom of the syringe barrel.

Thus, it is envisaged according to the invention to provide the syringe with a position-sensing device for the plunger moving inside the syringe barrel and connected to a plunger rod, wherein at least one magnet is fixed in a stationary manner relative to the syringe barrel and a magnetic field sensor is attached to the plunger rod to sense the magnetic field of the magnet.

This construction solves the problem of easily detecting, at reduced expenditure, whether the plunger is located at its end position, fully advanced into the syringe barrel. In this connection, sensing is effected in a contact-free manner, so that wear caused by contact, which is inevitable in a mechanical stop switch, no longer occurs.

The arrangement in which the magnet is fixed in a stationary manner relative to the syringe barrel and the magnetic field sensor is attached to the plunger rod, which is the opposite of the prior art arrangement, enables a surprisingly simple solution, wherein the plunger rod may remain unchanged as with syringes having no position-sensing device, in particular, at the plunger or at the plunger portion where the plunger rod is located inside the syringe barrel when being maximally advanced. Complex designs or alterations of the plunger rod as required for known position-sensing devices using the magnetic principle can be dispensed with completely.

Contrary to conventional syringes, i.e. syringes operating without a position-sensing device, the plunger rod may remain completely unchanged by simply fitting the magnetic field sensor to the plunger rod at its end facing away from the plunger. In particular, a plunger rod extension carrying the magnetic field sensor may be used. In a particularly convenient further embodiment, the magnetic field sensor is directly connected with a circuit also attached to the plunger rod, said circuit processing the signal from the magnetic field sensor and emitting an output signal, which indicates whether the plunger is maximally advanced into the syringe barrel. Said circuit may be part of the plunger rod extension.

The described further embodiment of the circuit is further advantageous in that contacting is required only via three conductors; two of said conductors serve to supply power to the circuit and a third conductor transmits the output signal, which is preferably a binary signal.

The circuit may be of a particularly small construction, if the signal from the magnetic field sensor is, for a predetermined minimum field strength, greater than a threshold value, and the position and the coercive force of the magnet as well as the position of the magnetic field sensor at the end of the plunger rod are selected such that the signal from the magnetic field sensor exceeds the threshold value only if the plunger abuts inside the syringe barrel. The magnet, which is arranged in a stationary manner relative to the syringe barrel, as well as the magnetic field sensor comprising said circuit will then function in the manner of a reed contact.

In this embodiment, the arrangement of the magnet is to be selected to correspond to the sensitivity of the magnetic field sensors and to the circuit design. A particularly simple construction is achieved by arranging the magnet in the region of a plunger rod guide through which the plunger rod extends into the syringe barrel.

The signal from the magnetic field sensor makes it possible to very simply provide a control unit causing the syringe barrel to be filled when the output signal indicates a maximally advanced plunger in the syringe barrel.

DESCRIPTION OF THE DRAWINGS

The invention is explained in more detail below, by way of example and with reference to the drawings, wherein.

DETAILED DESCRIPTION

Figure 1:
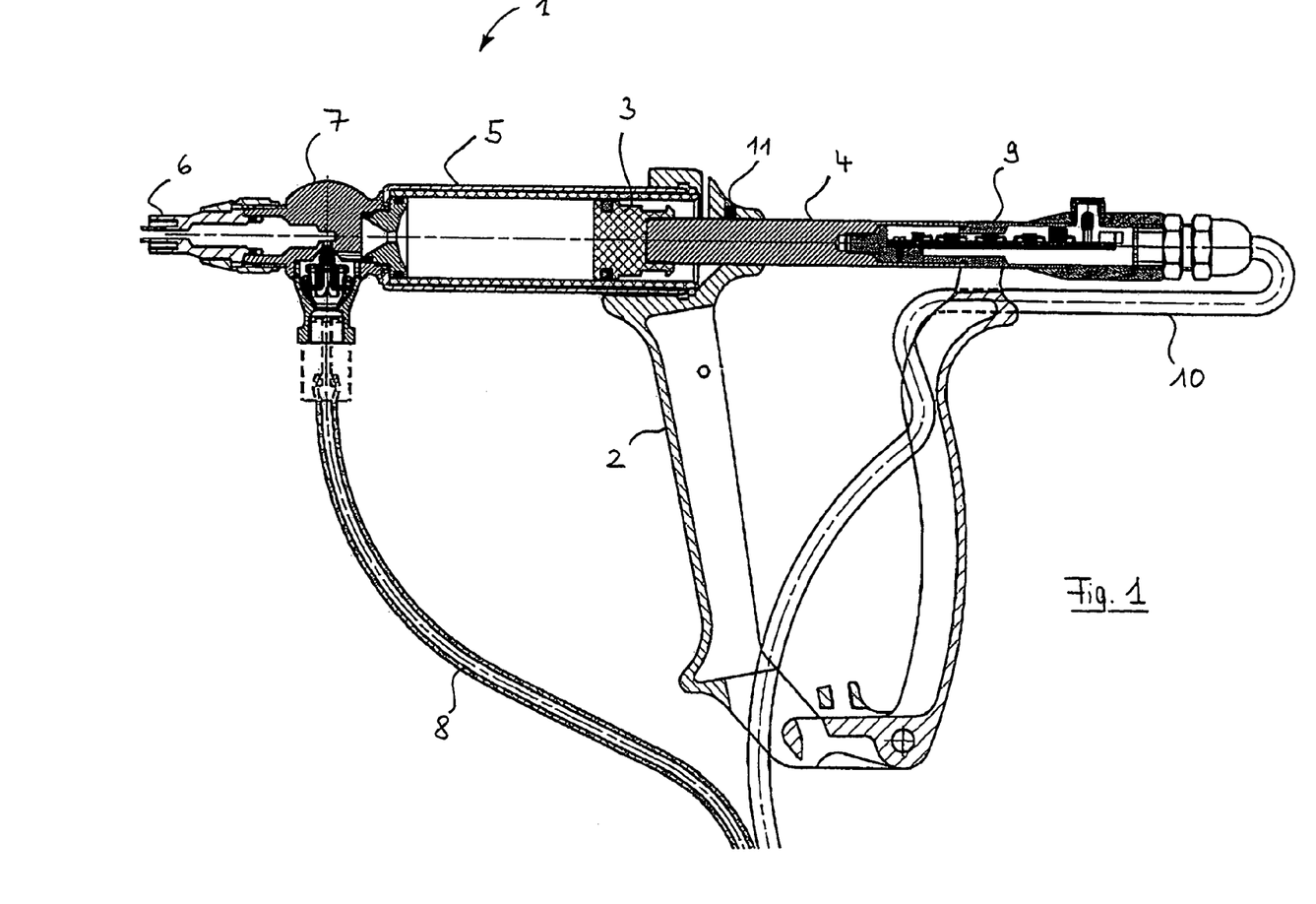
FIG. 1 shows a schematic sectional view of a veterinary syringe.

FIG. 1 shows a veterinary syringe 1 in a sectional representation. The syringe 1 comprises a handle 2 having applied thereto a lever by which the syringe can be actuated. Actuation of the lever acts on a plunger 3 which is attached to a plunger rod 4 and moves inside a barrel 5. The syringe further comprises a port 6 onto which a syringe needle may be fitted. A port 6 is screwed onto a syringe head 7 by means of an intermediate ring. On an opposite side, a barrel 5 is screwed into the head using a suitable gasket. Further, a supply duct 8 from a fluid container (not shown in FIG. 1), which is connected to a fluid container port of the syringe head 7, terminates in the syringe head 7 via a valve mechanism without a reference numeral in FIG. 1, which will be explained later.

A position-sensing device 9, which is electrically connected via a signal cable and cooperates with a magnet 11 provided at the end of the handle 2 into which the syringe barrel is inserted, in order to detect, whether the plunger 3 is maximally advanced into the barrel 5, i.e. whether the barrel 5 is empty, is fitted onto the end of the plunger rod 4 located opposite the plunger 3.

Figure 2:
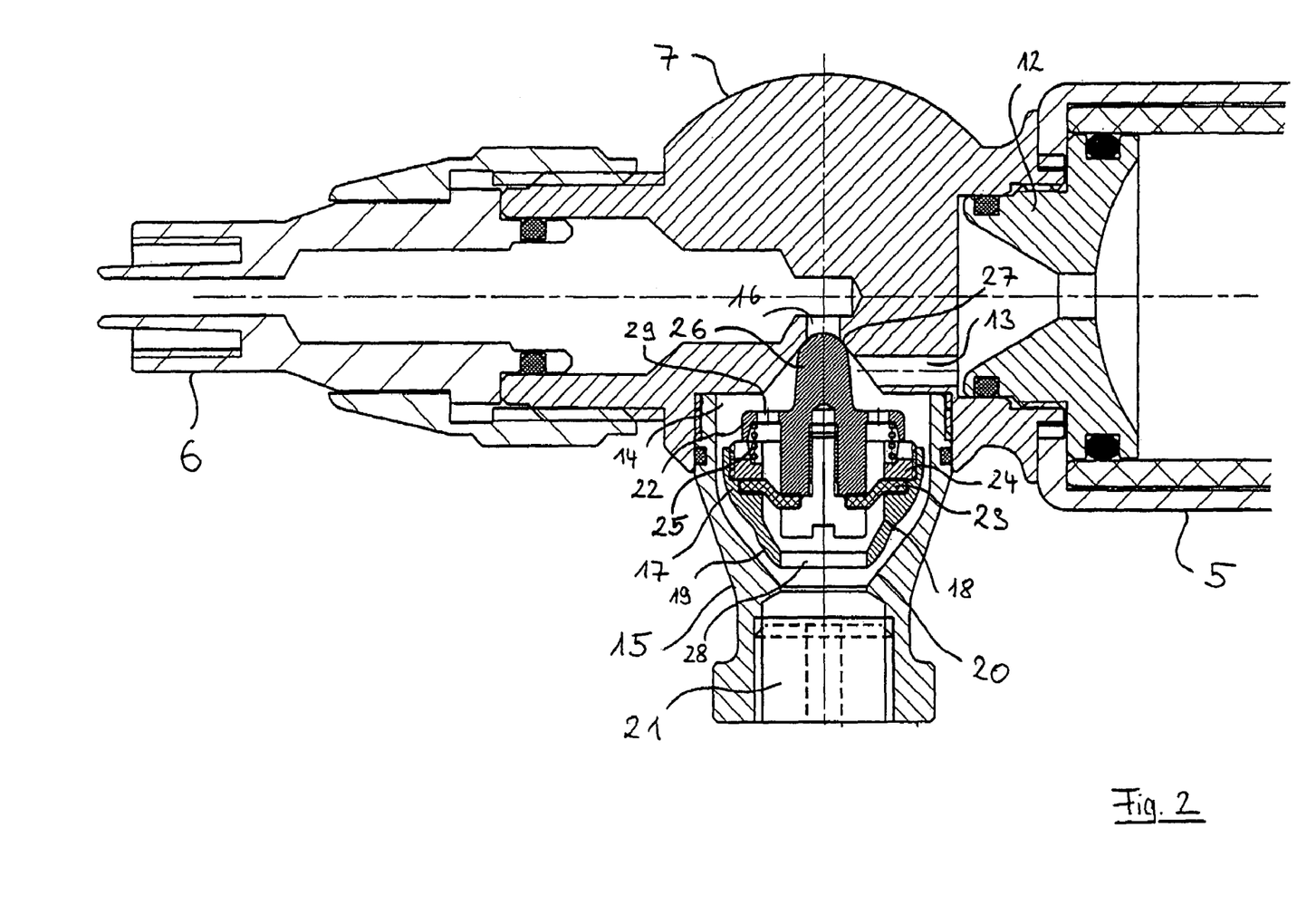
FIG. 2 shows an enlarged sectional view of the syringe of FIG. 1 in the region of the valve mechanism, with a valve member being located in a first position, in which fluid flow from a fluid container port to a syringe barrel is possible and, at the same time, fluid flow from the syringe barrel to a discharge outlet is not possible.

FIG. 2 shows a detail of the syringe 1 of FIG. 1 in the region of the syringe head 7. As can be seen, the barrel 5 is attached to the syringe head 7 by means of a gasket screwed into the syringe head 7. The gasket has a bore and thus acts as a restrictor 12. The thus-formed outlet through the restrictor 12 at the bottom of the barrel 5 opens into a barrel outlet 13 formed by a bore extending into a valve chamber 14. The valve chamber 14 is formed by the syringe head 7 and a valve housing 15 screwed into the head. A discharge channel 16 for connection opens into the valve chamber 14. In FIG. 2, a valve member 17 closes the discharge channel 16. The valve member 17 comprises a lower part 18 having a sealing surface 19, which is shown in FIG. 2 in a position spaced apart from a valve seat 20.

Thus, the valve chamber 14 is formed by a valve housing 15, which is screwed into the syringe head 7 in a sealing manner, so that the valve chamber 14 is formed by the syringe head 7, having a discharge channel 16 formed therein, extending toward the port 6, and by the barrel outlet 13, extending toward the barrel 5, as well as by the valve housing 15.

The valve seat 20 is part of a supply port 21, which is formed in the valve housing 15 and which connects to a fluid container (not shown). In the position of the valve member 17 shown in FIG. 2, fluid can flow from the supply port 21, past the sealing surface 19 and the valve seat 20, to the barrel outlet 13 and, from there, through the restrictor 12 into the barrel. The discharge channel 16 is sealed, at the same time, by an upper part 22 of the valve member 17, so that no fluid can flow to the port 6. The upper part 22 is fitted on a plate 23, which is attached to the lower part 18 of the valve member 17 by a ring 24. Further, between said upper and lower parts, there extends a spring 25, which biases the lower part 17 away from the upper part 22 together with the plate 23, which has elastic properties.

The compressed shape of the valve member 17 shown in FIG. 2, in which the upper part 22 and the lower part 18 are pressed upon each other by the elastic force of the plate 23 and of the spring 25, is achieved by pressurized fluid being supplied via the supply port 21. Said fluid flows into the barrel 5; the discharge channel 16 is sealed by a nose 26 which is formed on the upper part 22 and is in sealing contact with a taper bore 27 of the discharge channel 16. Since the barrel outlet 13 opens into the valve chamber 14 between the sealing surface 19 and the taper bore 27, fluid flows from the supply duct 21 into the barrel 5, i.e. the barrel 5 is filled from the fluid container, in the condition shown in FIG. 2.

In order to adjust the pressure required to compress the valve member 16 into the position shown in FIG. 2, an opening 28 is provided in the lower part 18, through which fluid may also exert pressure on the bottom surface of the upper part 18. For the same reason, the upper part 22 of the valve member 17 also comprises openings 29, whose size is a decisive factor for the pressure exerted by the upper surface and required in order to leave the position of FIG. 2.

FIG. 2 shows a first position, in which fluid can flow from the fluid container port 21 to the barrel 5, but not between the barrel 5 and the discharge outlet 6 or between the fluid container port 21 and the discharge outlet 6.

Figure 3:
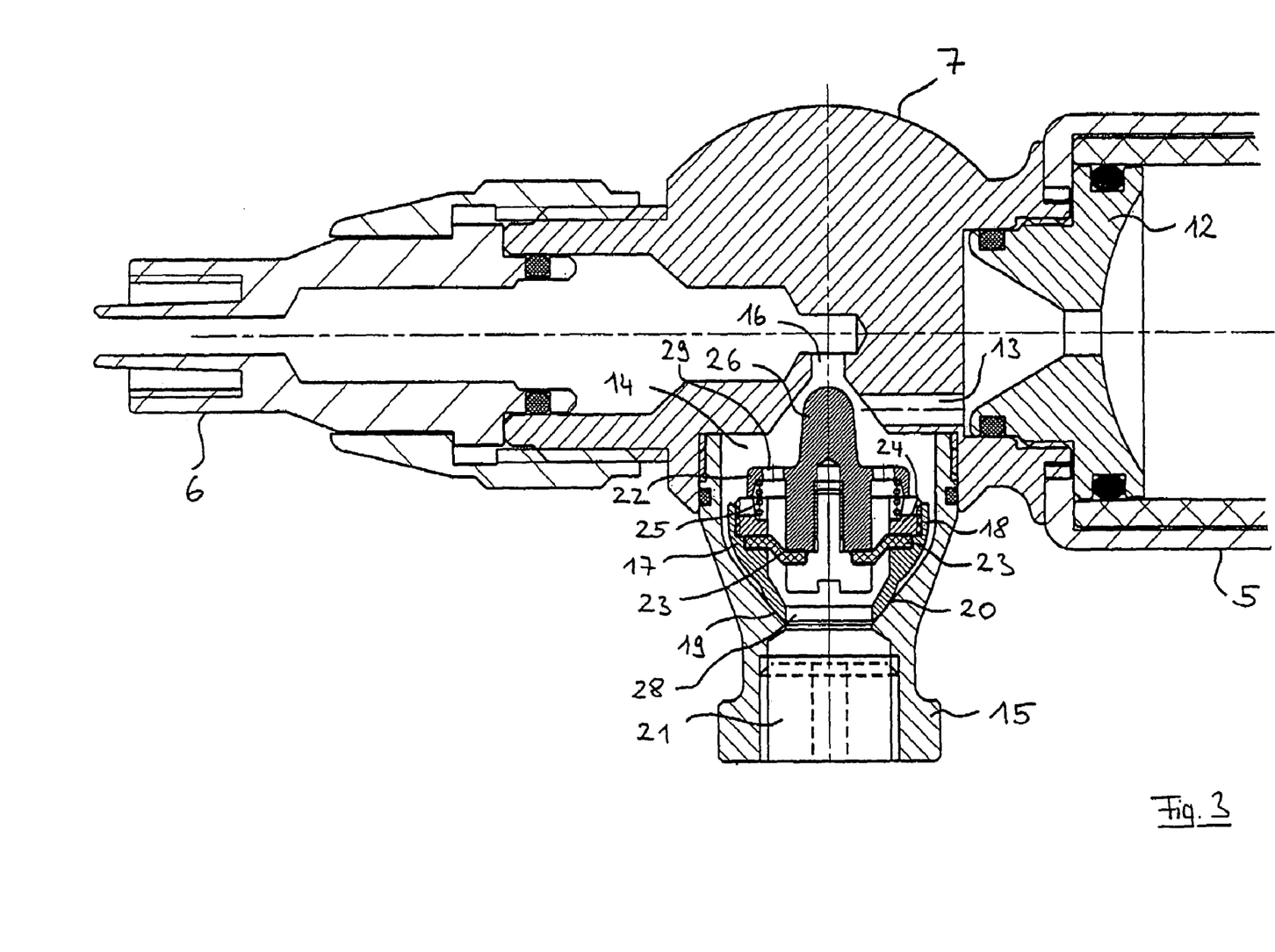
FIG. 3 shows the same view as FIG. 2, wherein the valve member is now in a second position, in which fluid flow from the syringe barrel to the discharge outlet is possible and, at the same time, fluid flow between the fluid container port and the syringe barrel is blocked.

In a second position, fluid flow is possible only between the barrel 5 and the discharge outlet 6; this position of the valve member 17 is shown in FIG. 3. It corresponds substantially to the position of FIG. 2, but now, the entire valve member 17 is still pressed down onto the valve seat 20 with the upper part 22 being pressed onto the lower part 18. This condition is achieved if there is no more overpressure at the supply port 21, but the plunger is being pushed forward inside the barrel 5, so that pressurized fluid flows from the barrel outlet 13 and into the valve chamber 14. The pressure acting on the upper part 22 of the valve member 17 has the effect, on the one hand, that the upper part 22 is pushed toward the lower part 18 and, on the other hand, that the sealing surface 19 of the lower part 18 comes to rest on the valve seat 20. As a result, no fluid flow is possible from the valve chamber 14 to the supply port 21. Instead, fluid flows from the barrel 5, via the restrictor 12, the barrel outlet 13 and the discharge channel 16, to the port 6 and, from there, out of the syringe 1.

Figure 4:
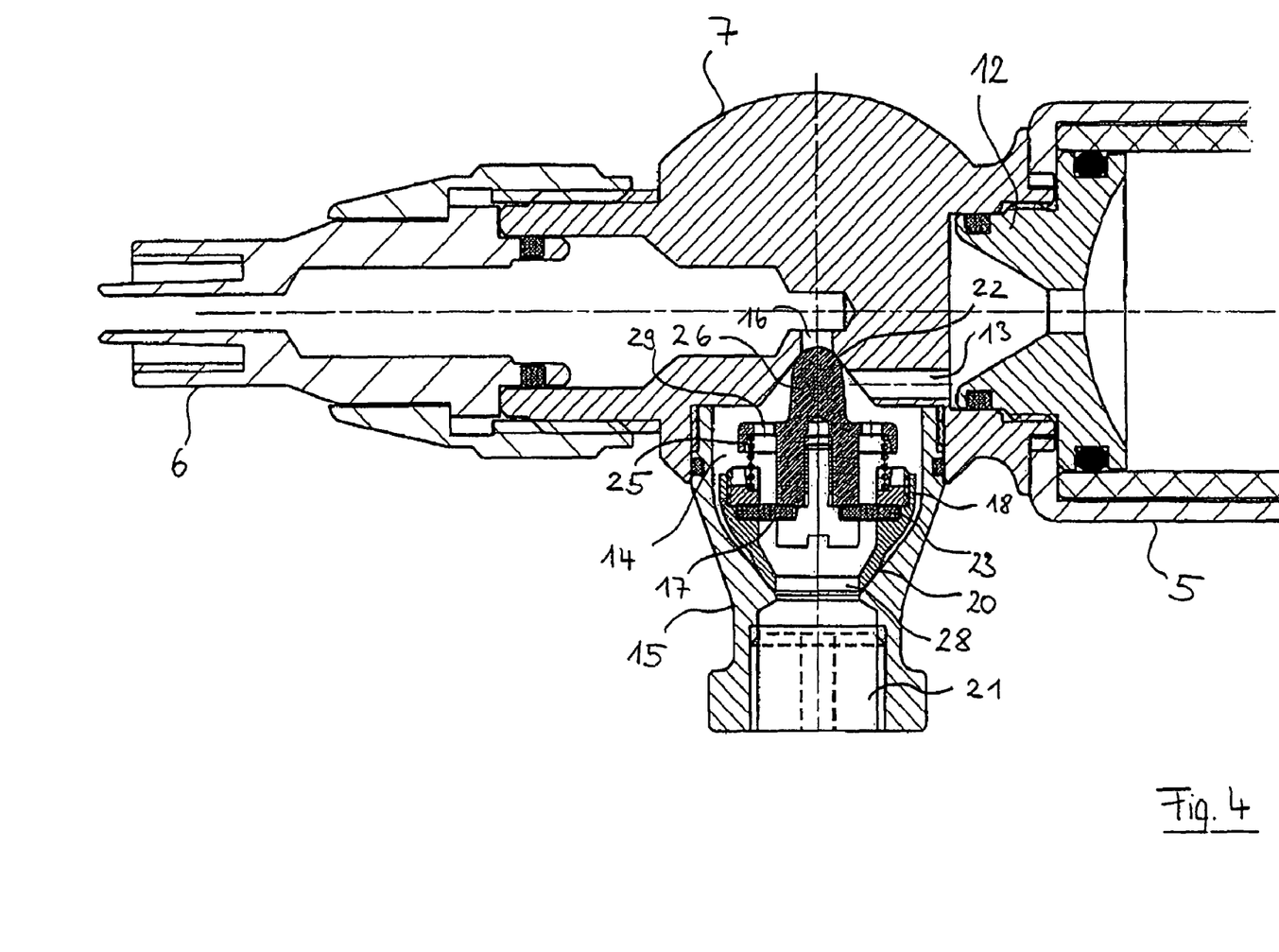
FIG. 4 shows the same view as FIGS. 2 and 3, with the valve member being in a third position, in which the supply duct to the fluid container port, the discharge outlet and the syringe barrel are not in fluid communication with each other.

If there is no increased pressure at the supply port 21 nor at the syringe barrel 5, this will result in the third position of the valve member shown in FIG. 4. The spring 25 as well as the elastic plate 23 expand the valve member 17 in that the upper part 22 is pushed away from the lower part. As a consequence, the lower part 18 is seated against the valve seat 20 by its sealing surface 19 and seals the valve chamber 14 to the supply port 21. Likewise, the nose 26 is seated in the taper bore 27 and blocks the discharge channel 16. Thus, the barrel outlet 13 and, consequently, the barrel 5, the discharge channel 16 (and also the port 6) as well as the supply port 21 (and the fluid container) are fluid-disconnected from each other. The valve member 17 may be moved either to the first position (FIG. 2) or to the second position (FIG. 3) by applying overpressure to the supply port 21 or by generating overpressure at the barrel outlet 13.

Figure 5:
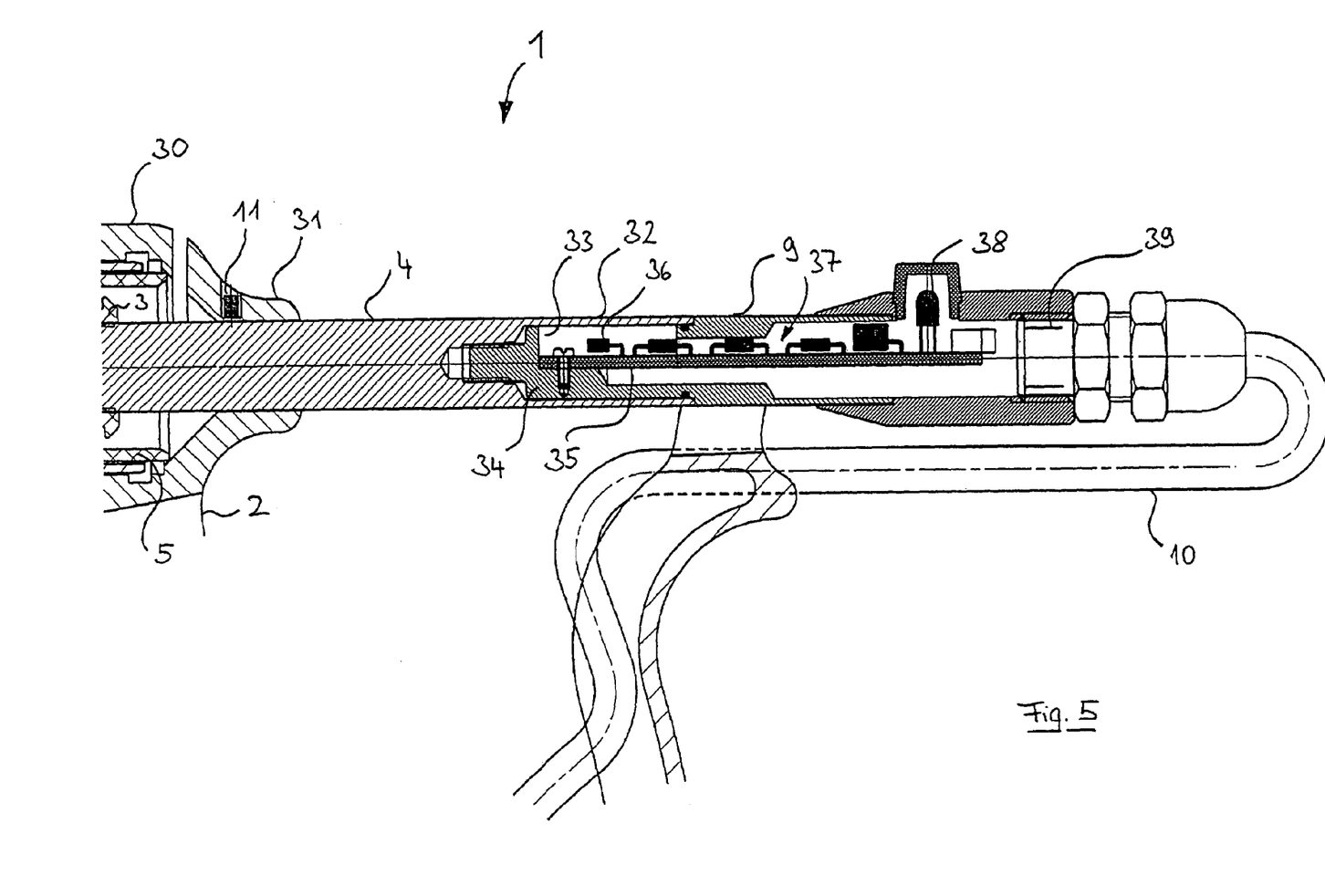
FIG. 5 shows an enlarged representation of the end of a plunger rod of the syringe, said plunger rod having fitted thereon a circuit comprising a magnetic field sensor.

FIG. 5 shows the position-sensing device 9 in an enlarged representation. The position-sensing device 9 emits a signal via the signal cable 10, indicating whether the plunger 3 is fully advanced into the barrel 5. FIG. 5 shows the end of the barrel 5 located opposite the syringe head 7, said end being held in a barrel reception 30 provided on the handle 2. The barrel reception 30 further comprises a plunger rod guide 31, by means of which the plunger rod 4 passes into the barrel 5.

A bore 33 is provided in the end 32 of the plunger rod 4 located opposite the plunger 3, said bore 33 receiving a printed circuit board carrier 34 which forms an extension of the plunger rod 4. The printed circuit board carrier 34 holds a printed circuit board 35 provided with a Hall sensor 36 thereon, which senses the fields of three magnets, of which only one magnet 11 is shown in the sectional view of FIG. 5. The magnets are inserted in suitable bores in the area of the plunger rod guide 31.

The Hall sensor 36 is connected with a circuit 37, which is located on the printed circuit board 35 and also comprises an LED 38, in addition to other components to be explained later. The LED 38 indicates whether the position-sensing device 9 is activated. The circuit 37 on the printed circuit board 35 comprising the Hall sensor 36 and the LED 38 is connected to the signal cable 10 via a plug connection 39.

Figure 6:
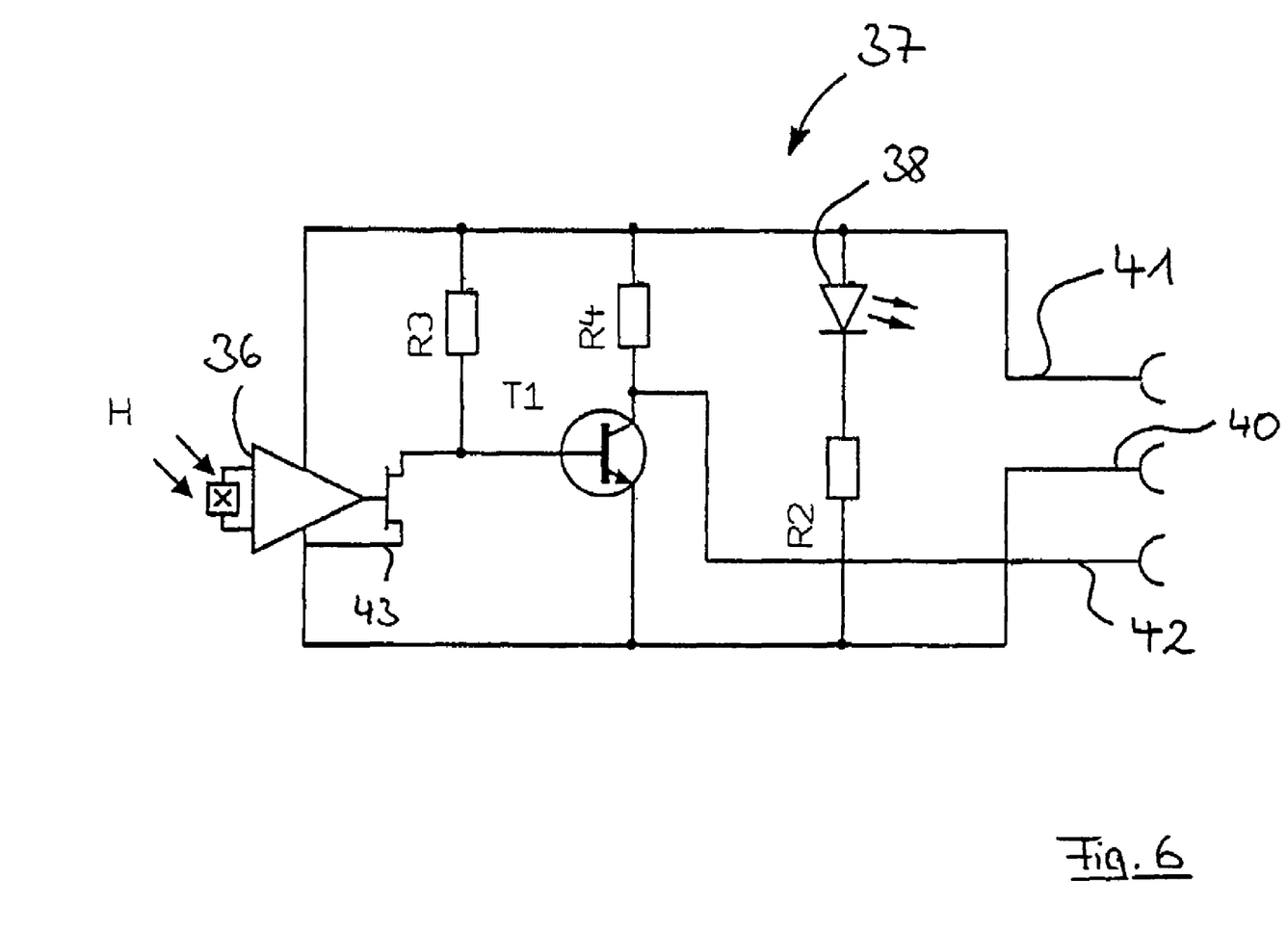
FIG. 6 shows a circuit diagram for the circuit of FIG. 5.

FIG. 6 shows the circuit diagram of the circuit 37. The Hall sensor 36 of the circuit 37 is provided as an active component which is connected to a Gnd terminal 40 and a Vcc terminal 41 for power supply. The output of the Hall sensor 36, which senses the magnetic field symbolized as H in FIG. 6, is applied to the gate of a FET 43 whose drain-source path extends from the potential of the Gnd terminal 40 to the base of a transistor T1. In a convenient realization, the Hall sensor 36 and the FET 43 are comprised in one component, and the transistor T1 is, for example, of the BC547C type.

The base of the transistor T1 further has a resistor R3 applied thereto, having a resistance of, for example, 4.7 kΩ, whose other pole is on the potential of the Vcc terminal. The emitter of the transistor T1 is applied to Gnd potential, whereas the collector is connected with a signal output 42. In order to cause this signal output 42 to rise to Vcc during blocking of the transistor T1, the collector of the transistor T1 is additionally connected to Vcc via a resistor R4 (1 kΩ).

In order to allow a user to recognize whether the circuit 37 is supplied with supply voltage, i.e. whether the Hall sensor 36 can emit the required signal, the LED 38 is additionally connected with a suitable ballast resistor (e.g. 270), between Vcc and Gnd, so that a 10 mA current flows and the LED 38 lights up at Vcc=5 V.

Thus, in the circuit 37, the Hall sensor 36 switches the base of the transistor T1 to the potential of the Gnd terminal 40, via the FET 43, if the magnetic field H exceeds a certain threshold value. Said threshold value, and thus a non-conducting transistor T1, occurs when the plunger 3 is in the stop position inside the barrel 5, i.e. when the barrel 5 has been emptied. Only then is the magnetic field H of the magnet 11 large enough to cause the Hall sensor 36 and, thus, the circuit 37 to switch over. If the plunger 3 is not in the stop position, the transistor T1 is conducting, and the signal at the signal output 42 of the circuit 37 is on a low level. The same applies if the circuit is not activated, i.e. if no supply voltage is applied to the Vcc terminal 41. The signal output 42 is then also on a low level, but now depending on the distance of the Hall sensor 36 from the magnet 11. At the same time, the LED 38 does not light up.

However, if the plunger 3 is in the stop position, i.e. if it is fully advanced into the barrel 5, the Hall sensor 36 is then approximated to the magnet 11, such that the magnetic field H causes the Hall sensor 36 to switch over; the FET 43 switches through, thus blocking the transistor T1. The output signal 42 is on the level of the Vcc terminal 41, i.e. high.

By monitoring the signal output 42, a control unit (not shown) can detect an empty barrel 5. A pressure increase at the supply port 21 then moves the valve member 17 into the first position shown in FIG. 2 and the barrel 5 is refilled.

What is claimed is:

1. A syringe comprising:
   a fluid container port for a fluid container containing fluid to be discharged,
   a syringe barrel with a plunger moving therein, and
   a discharge outlet, through which fluid supplied by actuation of the plunger in the fluid container port is dischargeable, wherein
   said syringe barrel is connected with the fluid container port and the discharge outlet via a fluid channel system,
   a valve mechanism is provided in the fluid channel system, allowing the syringe barrel to be filled with fluid supplied at the fluid container port and to then discharge said fluid through the discharge outlet, and
   the valve mechanism comprises a single valve member which is movable between first and second positions, said single valve member, in said first position, allowing fluid flow from the fluid container port to the syringe barrel and simultaneously blocking fluid flow from or to the discharge outlet and, in said second position, allowing fluid flow from the syringe barrel to the discharge outlet while simultaneously blocking fluid flow from or to the fluid container port, and including biasing means which bias the single valve member into a selected position.

2. Dosing syringe as claimed in claim 1, wherein the single valve member further comprises a third position in which the syringe barrel, the fluid container port and the discharge outlet are not in fluid communication with each other.

3. Syringe as claimed in claim 1 or 2, wherein the fluid channel system comprises a discharge channel from the syringe barrel to the discharge outlet, into which the fluid container port opens, with the valve member being arranged in the opening region.

4. Syringe as claimed in claim 1, wherein the single valve member has a first sealing surface, which closes the discharge channel to the discharge outlet in the first position, and a second sealing surface, which closes the fluid container port in the second position.

5. Syringe as claimed in claim 2, further comprising the biasing means biasing the single valve member into the third position in such a manner that the bias can be overcome by actuation of the plunger to move the valve member into the second position.

6. Syringe as claimed in claim 1, wherein the valve member is movable between both positions.

7. Syringe as claimed in claim 5, wherein the single valve member comprises an upper part including the first sealing surface, and a lower part including the second sealing surface, said upper part and said lower part being displaceable relative to one another and being pushed apart into the third position by the biasing means.

8. Syringe as claimed in claim 7, wherein the single valve member is arranged in a valve chamber forming one seat each for the first and second sealing surfaces and in which a fluid channel extending to the syringe barrel terminates.

9. Syringe as claimed in claim 1, wherein a fluid container is connectable with the fluid container port and is connected with a pressurizing means, so that the fluid may be pressurized in order to fill the syringe barrel with fluid.

10. Syringe as claimed in claim 1, further comprising a position-sensing device for the plunger moving inside the syringe barrel and connected with a plunger rod, which device includes at least one magnet being fixed in a stationary manner relative to the syringe barrel and a magnetic field sensor attached to the plunger rod to sense the magnetic field of the magnet.

11. Syringe as claimed in claim 10, wherein the magnetic field sensor is fitted to the plunger rod at its end facing away from the plunger.

12. Syringe as claimed in claim 10, wherein the magnetic field sensor is connected with a circuit, said circuit being also attached to the plunger rod and processing the signal from the magnetic field sensor and emitting an output signal, which indicates whether the plunger is maximally advanced into the syringe barrel.

13. Syringe as claimed in claim 12, wherein the signal from the magnetic field sensor exceeds a predetermined minimum field strength greater than a threshold value and wherein the position and coercive force of the magnet as well as the position of the magnetic field sensor are selected such that the threshold value is exceeded only if the plunger is fully advanced into the syringe barrel.

14. Syringe as claimed in claim 10, wherein the at least one magnet is located near a plunger rod guide.

15. Syringe as claimed in claim 9, further comprising a control unit causing the syringe barrel to be filled when the output signal indicates a fully advanced plunger.

16. Syringe as claimed in claim 12, further comprising a control unit causing the syringe barrel to be filled when the output signal indicates a fully advanced plunger.

17. Syringe as claimed in claim 16, wherein a fluid container is connectable with the fluid container port and is connected with a pressurizing means, so that the fluid may be pressurized in order to fill the syringe barrel with fluid.

* * * * *